United States Patent
Schoenafinger et al.

(10) Patent No.: US 6,900,233 B2
(45) Date of Patent: *May 31, 2005

(54) SUBSTITUTED 3-PHENYL-5-ALKOXY-3H-(1,3,4)-OXADIAZOL-2-ONES, PHARMACEUTICAL COMPOSITION AND METHOD FOR TREATING OBESITY THEREOF

(75) Inventors: Karl Schoenafinger, Alzenau (DE); Stefan Petry, Frankfurt (DE); Günter Müller, Sulzbach a. Ts. (DE); Armin Bauer, Sulzbach (DE); Hubert Otto Heuer, Schwabenheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 49 days.

This patent is subject to a terminal disclaimer.

(21) Appl. No.: 10/375,247

(22) Filed: Feb. 27, 2003

(65) Prior Publication Data

US 2003/0181433 A1 Sep. 25, 2003

Related U.S. Application Data

(60) Provisional application No. 60/365,706, filed on Mar. 19, 2002.

(30) Foreign Application Priority Data

Feb. 28, 2002 (DE) .......................... 102 08 987

(51) Int. Cl.$^7$ ............... A61K 31/4245; C07D 271/113; A61P 3/00
(52) U.S. Cl. ...................... 514/364; 548/144
(58) Field of Search ................... 514/364; 548/144

(56) References Cited

U.S. PATENT DOCUMENTS 4,150,142 A    4/1979  Boesch
5,093,343 A *  3/1992  Bonse et al. ............. 514/363
5,236,939 A    8/1993  Bonse
6,369,088 B2 * 4/2002  Schoenafinger et al. .... 514/364
6,596,742 B1 * 7/2003  Petry et al. ............. 514/364

FOREIGN PATENT DOCUMENTS

| DE | 2603877 | 8/1976 |
|---|---|---|
| DE | 2604110 | 8/1976 |
| EP | 0048040 | 8/1984 |
| EP | 0067471 | 11/1985 |
| EP | 0419918 | 4/1991 |
| WO | WO 01/17981 | 3/2001 |
| WO | WO 01/66531 | 9/2001 |

OTHER PUBLICATIONS

1985, CAS:103:178266.*

* cited by examiner

Primary Examiner—Rita Desai
Assistant Examiner—Robert Shiao
(74) Attorney, Agent, or Firm—Joseph D. Rossi

(57) ABSTRACT

A substituted 3-phenyl-5-alkoxy-3H-(1,3,4)-oxadiazol-2-one, compound of formula 1,

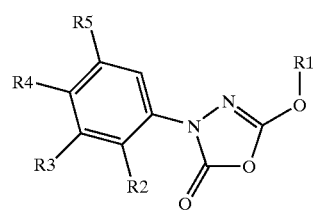

wherein $R^1$, $R^2$, $R^3$, $R^4$ and $R^5$ are as defined herein, pharmaceutical composition comprising the compound and use of the compound for inhibiting pancreatic lipase, or the prophylaxis or treatment of obesity are described.

11 Claims, No Drawings

SUBSTITUTED 3-PHENYL-5-ALKOXY-3H-(1,3,4)-OXADIAZOL-2-ONES, PHARMACEUTICAL COMPOSITION AND METHOD FOR TREATING OBESITY THEREOF

FIELD OF THE INVENTION

The invention relates to substituted 3-phenyl-5-alkoxy-3H-(1,3,4)-oxadiazol-2-ones. The invention further relates to a pharmaceutical composition that comprises a substituted 3-phenyl-5-alkoxy-3H-(1,3,4)-oxadiazol-2-one. The invention further relates to a method for the prophylaxis or treatment of obesity, or inhibiting pancreatic lipase, PL, in a patient wherein such could be useful comprising administering to the patient a pharmaceutically effective amount of a substituted 3-phenyl-5-alkoxy-3H-(1,3,4)-oxadiazol-2-one.

BACKGROUND OF THE INVENTION

Certain 5-alkoxy-1,3,4-oxadiazol-2-ones with an ortho-substituted phenyl ring as substituent or with fused-on five- or six-membered rings have an anthelmintic (DE-A 26 04 110) and insecticidal action (DE-A 26 03 877, EP-B 0 048 040, EP-B 0 067 471).

Certain 5-phenoxy-1,3,4-oxadiazol-2-ones with an ortho-substituted phenyl ring as substituent show an endoparasiticidal action (EP-A 0 419 918).

Substituted 3-phenyl-5-alkoxy-3H-(1,3,4)-oxadiazol-2-ones with an inhibitory effect on hormone-sensitive lipase are disclosed in WO 01/17981 and WO 01/66531.

SUMMARY OF THE INVENTION

The invention is directed to compounds that evidence an inhibitory effect on pancreatic lipase, PL.

A useful compound according to the invention is the substituted 3-phenyl-5-alkoxy-3H-(1,3,4)-oxadiazol-2-one of formula 1,

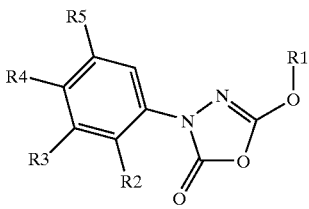

wherein:

$R^1$ is $C_7$–$C_{22}$-alkyl;

$C_4$–$C_{20}$-alkoxy-, $C_6$–$C_{10}$-aryl-, $C_6$–$C_{10}$-aryloxy- or $C_4$–$C_{12}$-alkoxy-$C_2$–$C_4$-alkoxy-substituted $C_2$–$C_4$-alkyl, wherein the aryl is a phenyl or naphthyl that is substituted one or more times by halogen, $C_1$–$C_9$-alkyl, $C_1$–$C_8$-alkyloxy, nitro or $CF_3$, $C_7$–$C_{20}$-alkenyl;

3β-cholestan-3-yl; or phenyl that is substituted by $C_6$–$C_{12}$-alkyl or phenoxy; and $R^2$, $R^3$, $R^4$ and $R^5$ are each, independently, hydrogen;

halogen;

nitro;

amino;

$CF_3$;

$OCF_3$;

$C_1$–$C_4$-alkyl, $C_1$–$C_9$-alkyloxy, $C_6$–$C_{10}$-aryl-$C_1$–$C_4$-alkyloxy, $C_6$–$C_{10}$-aryloxy, $C_6$–$C_{10}$-aryl, $C_1$–$C_4$-alkylamino, di-$C_1$–$C_4$-alkyl-amino, or $C_1$–$C_4$-alkylcarbonylamino, wherein the alkyl is optionally substituted one or more times by halogen, hydroxy, di-$C_1$–$C_4$-alkylamino, $CF_3$, $C_1$–$C_4$-alkyloxy or $C_1$–$C_4$-alkyl, and the aryl is optionally substituted one or more times by halogen, $C_1$–$C_9$-alkyl, $C_1$–$C_8$-alkyloxy or $CF_3$; or $C_3$–$C_8$-cycloalkyl or $C_3$–$C_8$-cycloalkyloxy, wherein the cycloalkyl is optionally substituted one or more times by halogen, $CF_3$, $C_1$–$C_4$-alkyloxy, $C_1$–$C_4$-alkyl or $C_6$–$C_{10}$-aryl;

or a prodrug, solvate, pharmaceutically acceptable basic salt or acid addition salt thereof.

DETAILED DESCRIPTION OF THE INVENTION

Definition of Terms

As used above, and throughout the description of the invention, the following terms, unless otherwise indicated, shall be understood to have the following meanings.

Halogen is fluorine, chlorine or bromine, preferably fluorine or chlorine.

Alkyl, alkenyl and alkoxy as used herein may be branched or unbranched.

Patient includes both human and other mammals.

Pharmaceutically effective amount means an amount of the compound according to the invention effective in producing the desired therapeutic effect.

Particular or Preferred Embodiments

A particular embodiment for $R^1$ as aryl is wherein the aryl is optionally substituted by halogen, $C_1$–$C_4$-alkyl, $C_1$–$C_4$-alkyloxy, nitro or $CF_3$.

A particular embodiment for $R^2$, $R^3$, $R^4$ or $R^5$ that encompasses aryl or alkyl is wherein the aryl and alkyl are optionally substituted one, two or three times by halogen, $CF_3$, $C_1$–$C_4$-alkyloxy or $C_1$–$C_4$-alkyl.

A particular embodiment for $R^2$, $R^3$, $R^4$ or $R^5$ that encompasses cycloalkyl is wherein the cycloalkyl is optionally substituted one, two or three times by halogen, $CF_3$, $C_1$–$C_4$-alkyloxy or $C_1$–$C_4$-alkyl.

A preferred compound according to the invention is a compound of formula 1 wherein: $R^1$ is $C_7$–$C_{22}$-alkyl, $C_7$–$C_{20}$-alkenyl, 3β-cholestan-3-yl or phenyl that is substituted by $C_6$–$C_{12}$-alkyl or phenoxy.

A further preferred compound according to the invention is a compound of formula 1 wherein: $R^2$ is hydrogen, halogen, $C_1$–$C_4$-alkyl, or $C_1$–$C_9$-alkyloxy.

A further preferred compound according to the invention is a compound of formula 1 wherein: $R^3$ is hydrogen, $C_1$–$C_4$-alkyl, $OCF_3$, or $C_6$–$C_{10}$-aryl-$C_1$–$C_4$-alkyloxy, wherein the aryl is optionally substituted by halogen.

A further preferred compound according to the invention is a compound of formula 1 wherein: $R^4$ is hydrogen, $OCF_3$ or chlorophenoxy.

A further preferred compound according to the invention is a compound of formula 1 wherein: $R^5$ is hydrogen.

A particularly preferred compound according to the invention is a compound of formula 1 wherein $R^1$ is $C_8$–$C_{16}$-alkyl.

A very particularly preferred compound according to the invention is a compound of formula 1 wherein:

$R^1$ is $C_8$–$C_{16}$-alkyl;

$R^2$ is hydrogen;
$R^3$ is hydrogen or $OCF_3$;
$R^4$ is hydrogen, $OCF_3$ or 4-chlorophenoxy; and
$R^5$ is hydrogen.

Very particularly preferred species according to the invention is that of formula 1, which is:
5-Dodecyloxy-3-(4-trifluoromethoxy-phenyl)-3H-(1,3,4)-oxadiazol-2-one;
5-Hexadecyloxy-3-(4-trifluoromethoxy-phenyl)-3H-(1,3,4)-oxadiazol-2-one;
5-Octyloxy-3-(4-trifluoromethoxy-phenyl)-3H-(1,3,4)-oxadiazol-2-one;
5-Hexadecyloxy-3-(3-trifluoromethoxy-phenyl)-3H-(1,3,4)-oxadiazol-2-one;
5-Hexadecyloxy-3-(4-(4-chlorophenoxy)-phenyl)-3H-(1,3,4)-oxadiazol-2-one;
5-Octyloxy-3-phenyl-3H-(1,3,4)-oxadiazol-2-one; or
5-Tetradecyloxy-3-(4-trifluoromethoxy-phenyl)-3H-(1,3,4)-oxadiazol-2-one.

The invention also encompasses all combinations of particular and preferred aspects of the invention noted herein.

It will be apparent to those skilled in the art that certain compounds of formula 1 can exhibit isomerism, for example geometrical isomerism, e.g., E or Z isomerism, and optical isomerism, e.g., R or S configurations. Geometrical isomers include the cis and trans forms of compounds of the invention having alkenyl moieties. Individual geometrical isomers and stereoisomers, including enantiomers and diastereoisomers, within formula 1, and their mixtures, are within the scope of the invention.

Pharmaceutically acceptable salts are particularly suitable for medical applications because of their greater solubility in water compared with the initial compounds on which they are based. These salts must have a pharmaceutically acceptable anion or cation. Suitable pharmaceutically acceptable acid addition salts of the compounds of the formula I are salts of inorganic acids such as hydrochloric acid, hydrobromic acid, phosphoric, metaphosphoric, nitric, sulfonic and sulfuric acids, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric and trifluoroacetic acids. It is particularly preferred to use the chloride salt and the tartaric acid salt for medical purposes. Suitable pharmaceutically acceptable basic salts are ammonium salts, alkali metal salts (such as sodium and potassium salts) and alkaline earth metal salts (such as magnesium and calcium salts). Salts with other anions such as perchlorate, hypochorite, tetrafluoroborate, hexachloroantimonate, picrate and azide, likewise fall within the scope of the invention as useful intermediates for preparing or purifying pharmaceutically acceptable salts and/or for use in non-therapeutic, for example in vitro, applications.

The term "physiologically functional derivative (prodrug)" used herein refers to any physiologically tolerated derivative of a compound according to the invention, for example an ester that is able on administration to a mammal, such as, for example, to humans, to form (directly or indirectly) such a compound or an active metabolite thereof. Such prodrugs can be metabolized in vivo to a compound of the formula 1. These prodrugs may themselves be active or not.

The compound of formula 1 may also exist in various polymorphous forms, for example as amorphous and crystalline polymorphous forms. All polymorphous forms of the compound of formula 1 fall within the scope of the invention and are a further aspect of the invention.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include ethanolates, methanolates, and the like.

The amount of a compound of formula 1 necessary to effect the method according to the invention, i.e., to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of body weight, for example 3–10 mg/kg/day. An intravenous dose may be, for example, in the range from 0.3 mg to 1.0 mg/kg, which can suitably be administered as infusion of 10 ng to 100 ng per kilogram and per minute. Infusion solutions suitable for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single dose formulations that can be administered orally, such as, for example, tablets or capsules, may contain, for example, from 1.0 to 1000 mg, typically from 10 to 600 mg. In the case of pharmaceutically acceptable salts, the above weight data are based on the weight of the salt of the compound of formula 1. The compound of formula 1 can be used as noted herein by itself, but it is preferably in the form of a pharmaceutical composition with a compatible carrier. The carrier must, of course, be compatible in the sense of compatibility with other ingredients of the composition and not be harmful to the patient's health. The carrier may be a solid or a liquid or both and is preferably formulated with the compound as single dose, for example as tablet, which may contain from 0.05% to 95% by weight of the active ingredient. Further an additional pharmaceutically active substance may likewise be present with the compound of formula 1. The pharmaceutical composition according to the invention is produced by one of the known pharmaceutical methods that essentially consist of mixing the ingredients with pharmacologically acceptable carriers and/or excipients.

Pharmaceutical compositions according to the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of the formula 1 used in each case. Coated formulations and coated slow-release formulations also fall within the scope of the invention. Acid- and gastric fluid-resistant formulations are preferred. Suitable gastric fluid-resistant coatings comprise cellulose acetate phthalate, polyvinyl acetate phthalate, hydroxypropylmethyl-cellulose phthalate and anionic polymers of methacrylic acid and methyl methacrylate.

Suitable pharmaceutical compounds for oral administration may be in the form of separate units such as, for example, capsules, cachets, pastilles or tablets, each of which contains a defined amount of the compound of the formula 1; as powder or granules; as solution or suspension in an aqueous or nonaqueous liquid; or as an oil-in-water or water-in-oil emulsion. These compositions may, as already mentioned, be prepared by any suitable pharmaceutical method that includes a step in which the active ingredient and the carrier (which may consist of one or more additional ingredients) are brought into contact. In general, the compositions are produced by uniform and homogeneous mixing of the active ingredient with a liquid and/or finely dispersed solid carrier, after which the product is shaped if necessary. Thus, for example, a tablet can be produced by compressing or shaping a powder or granules of the compound, where appropriate with one or more additional ingredients. Compressed tablets may be produced by tabletting the compound in free-flowing form, such as, for example, a powder or granules, where appropriate mixed with a binder, lubricant, inert diluent and/or one (or more) surface-active/dispersing agents in a suitable machine. Shaped tablets can be produced by shaping, in a suitable machine, the compound that is in powder form and has been moistened with an inert liquid diluent.

Pharmaceutical compositions suitable for peroral (sublingual) administration comprise suckable tablets that contain a compound of formula 1 with a flavoring, normally sucrose, and gum arabic or tragacanth, and pastilles that contain the compound in an inert base such as gelatin and glycerol or sucrose and gum arabic.

Suitable pharmaceutical compositions for parenteral administration comprise preferably sterile aqueous preparations of a compound of formula 1, which are preferably isotonic with the blood of the intended recipient. These preparations are preferably administered intravenously, although administration can also take place by subcutaneous, intramuscular or intradermal injection. These preparations can preferably be produced by mixing the compound with water and making the resulting solution sterile and isotonic with blood. Injectable compositions according to the invention generally contain from 0.1 to 5% by weight of the active compound.

Suitable pharmaceutical compositions for rectal administration are preferably in the form of single-dose suppositories. These can be produced by mixing a compound of formula 1 with one or more conventional solid carriers, for example cocoa butter, and shaping the resulting mixture.

Suitable pharmaceutical compositions for topical use on the skin are preferably in the form of an ointment, cream, lotion, paste, spray, aerosol or oil. Carriers that can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Suitable pharmaceutical compositions for transdermal applications may be in the form of single plasters that are suitable for long-term close contact with the patient's epidermis. Plasters of this type suitably contain the active ingredient in an aqueous solution that is buffered where appropriate, dissolved and/or dispersed in an adhesive or dispersed in a polymer. A suitable active ingredient concentration is about 1% to 35%, preferably about 3% to 15%. As a particular option, the active ingredient can be released by electrotransport or iontophoresis as described, for example, in Pharmaceutical Research, 2 (6): 318 (1986).

The compounds according to the invention of formula 1 can be prepared in various ways by methods known per se.

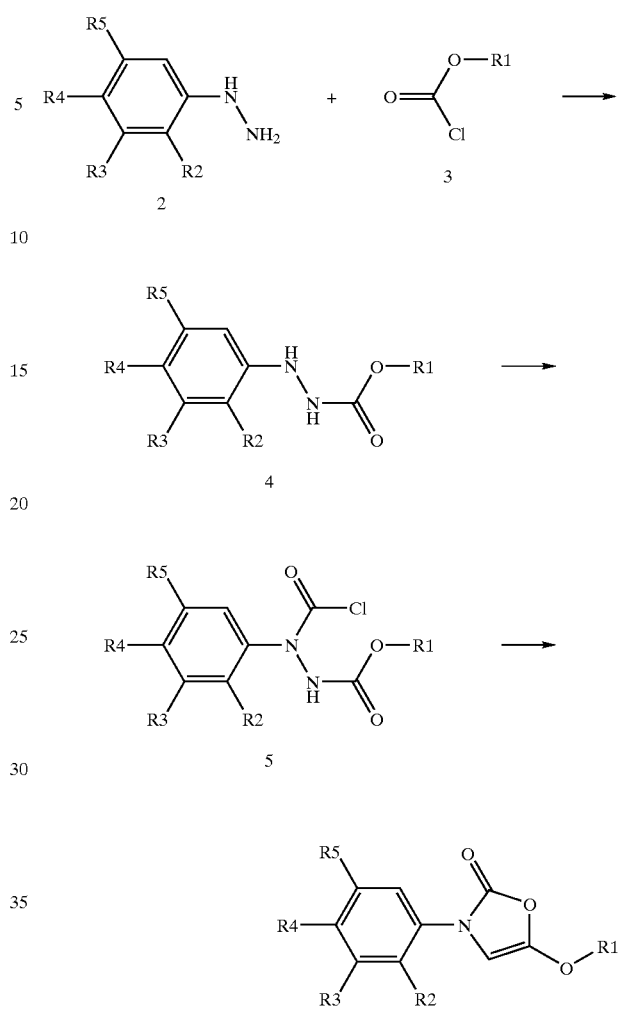

For example, substituted 3-phenyl-5-alkoxy-3H-(1,3,4)-oxadiazol-2-ones of formula 1 can be prepared by reacting a hydrazine of formula 2 with a chloroformic ester of formula 3 or other reactive carbonic ester derivative, wherein $R^1$, $R^2$, $R^3$, $R^4$ and $R^5$ are as defined above, to give a compound of formula 4, which is acylated with phosgene (for example, to give a compound of formula 5), carbonyldiimidazole, diphosgene or triphosgene, cyclized and converted where appropriate by further chemical modification of the radicals $R^2$–$R^5$, such as, for example, by reduction of nitro to amino radicals by known processes, and subsequent acylation or alkylation, into compounds of the formula 1. Since acids are usually liberated in these reactions, promotion is advisable by adding bases such as pyridine, triethylamine, sodium hydroxide solution or alkali metal carbonates. The reactions can be carried out in wide temperature ranges. It has proved advantageous as a rule to operate at 0° C. to the boiling point of the solvent used. Examples of solvents employed are methylene chloride, THF, DMF, toluene, ethyl acetate, n-heptane, dioxane, diethyl ether.

The hydrazines of formula 2 can be prepared by known methods, for example by diazotization of the corresponding anilines and

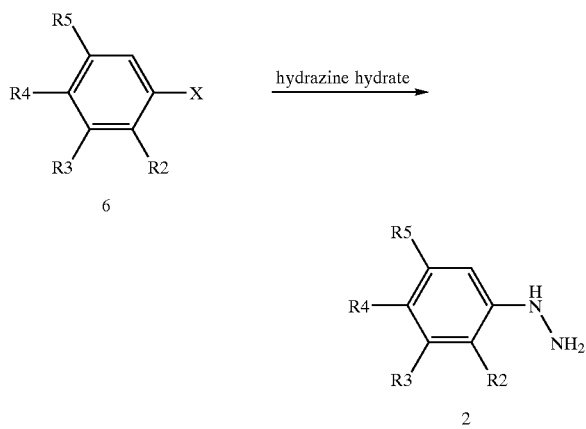

subsequent reduction by known methods or by nucleophilic substitution of suitably substituted phenyl derivatives 6 (X=F, Cl, Br, I, OSO$_2$CF$_3$) with hydrazine hydrate. Such suitable phenyl derivatives may be nitro-substituted halobenzenes, preferably fluoro- and chloronitrobenzenes, from which the compounds according to the invention can be prepared by known methods at a suitable point in the synthetic route by reduction and reaction with acylating or alkylating agents such as, for example, acid chlorides, anhydrides, isocyanates, chloroformic esters, sulfonyl chlorides or alkyl and arylalkyl halides, or by reductive alkylation with aldehydes.

The effect of the compounds according to the invention of formula 1 was tested using the following enzyme assay system: [lacuna]

The compounds of formula 1 show an inhibitory effect on pancreatic lipase (PL). As PL inhibitors, they are able to prevent absorption of fat consumed with the diet and thus lead to a reduction in the fat uptake and the body weight or prevent an increase in body weight. The compounds of formula 1 are particularly suitable for treating obesity but may also have a very beneficial effect in various metabolic derangements such as, for example, diabetes, and cardiovascular disorders such as, for example, hypertension and myocardial infarction.

The invention further relates to a method for the prophylaxis or treatment of obesity, in a patient in need thereof, comprising administering to the patient a pharmaceutically effective amount at least one compound of formula 1.

The activity of the compounds was assayed as follows:
1. Preparation of the Substrate:

80 µL of tripalmitin (85 mM in chloroform) are mixed with 5 µL of glycerol tri[9,10(n)-$^3$H]oleate (5 mCi/mL in toluene) in a 12 mL polypropylene vessel. Evaporation in a rotary evaporator (50° C.) and addition of 4 mL of 200 mM Tris/HCl (pH 7.6), 0.8% TX-100 are followed by ultrasound treatment of the mixture (Branson B-12 sonifier, output level 4, 3×2 min with 1 min intervals on ice) until a homogeneous milky suspension is produced.
2. Assay:

Lipase buffer: 80 mM Tris/HCl (pH 7.6), 600 mM NaCl, 8 mM CaCl$_2$, 8 mM benzamidine, 2 mM Pefabloc (Roche Biochemicals) (add the inhibitors only on the day of the assay)

Pancreatic lipase: Enriched preparation from porcine pancreas (Sigma order No. L-0382) dissolved in lipase buffer (100 000 units/500 µL)

Procedure:

5 µL of test substance (in 100% DMSO) or DMSO (control) are mixed with 10 µL of substrate and 5 µL of lipase (in this sequence) and incubated at 30° C. (Eppendorf Thermomixer, 350 min$^{-1}$) for 30 min. After addition of 325 µL of methanol/chloroform/n-heptane (10/9/7) and 105 µl of 0.1 M K$_2$CO$_3$, 0.1 M H$_3$BO3 (pH 10.5 adjusted with 1 M KOH) and vigorous mixing, the phases are separated by centrifugation (8000 rpm, Eppendorf centrifuge, 4° C.). 140 µL portions of the aqueous supernatant (contains the liberated radiolabeled oleate; 70% recovery) are transferred into 20 mL scintillation vials and mixed with 6 mL of scintillation cocktail (Beckman ReadySafe). After vigorously mixing and incubating at room temperature for 2 h, the radioactivity is measured in a liquid scintillation counter (Beckman, L8008, tritium channel with quench curve, measurement time 20 min).

Evaluation:

Substances are routinely tested in each concentration in three independent incubation mixtures each with duplicate determination after phase separation (SD<0.02). Background values (reaction under the same conditions but without lipase) are subtracted from all values (corresponds predominantly to the content of glycerol trioleate or free oleate in the substrate preparation in the aqueous phase, <5% of the radioactivity employed). The inhibition of the pancreatic lipase enzymatic activity by a test substance is determined by comparison with an uninhibited control reaction (presence of lipase=0% inhibition; absence of lipase 100% inhibition in each case after background correction). The IC$_{50}$ is calculated from an inhibition plot with up to 8 concentrations of the test substance. The software package GRAPHIT (Elsevier-BIOSOFT) is used for curve fitting and IC$_{50}$ determination.

The compounds showed the following effect in this assay:

| Compound Example No.: | IC$_{50}$ (µM) |
|---|---|
| 1 | 0.03 |
| 2 | 0.25 |
| 3 | 0.35 |
| 4 | 2.5 |
| 5 | 2.0 |
| 6 | 0.9 |
| 15 | 0.6 |

The following examples illustrate the preparation methods in greater detail without restricting them.

EXAMPLES

Example 1

5-Dodecyloxy-3-(4-trifluoromethoxy-phenyl)-3H-(1,3,4)-oxadiazol-2-one 0.43 mL of dodecyl chloroformate was cautiously added dropwise to a mixture consisting of 0.84 g of 4-trifluoromethoxyphenylhydrazine, 15 mL of NMP and 2 mL of pyridine while cooling in ice, and the mixture was then stirred for 2 hours while slowly warming to room temperature. After dilution with 50 mL of water, extraction by shaking was carried out with 30 mL of methylene chloride, the organic phase was dried with sodium sulfate and, while stirring and cooling in ice, 5 mL of pyridine and 3 mL of a 20% strength solution of phosgene in toluene were added dropwise. This mixture was allowed to stand overnight at room temperature and was diluted with a further 10 mL of methylene chloride and then washed 3 times with water. After drying over sodium sulfate, the mixture was concentrated in vacuo and the product was purified by column chromatography (silica gel, solvents:methanol:methylene chloride=2:98).

Yield: 0.85 g, M.p.: 41° C.

The compounds of the following examples were prepared analogously:

Example 2

5-Hexadecyloxy-3-(4-trifluoromethoxy-phenyl)-3H-(1,3,4)-oxadiazol-2-one

M.p.: 56° C.

Example 3

5-Octyloxy-3-(4-trifluoromethoxy-phenyl)-3H-(1,3,4)-oxadiazol-2-one

M.p.: oil

Example 4

5-Hexadecyloxy-3-(3-trifluoromethoxy-phenyl)-3H-(1,3,4)-oxadiazol-2-one

M.p.: 53° C.

Example 5

5-Hexadecyloxy-3-(4-(4-chlorophenoxy)-phenyl)-3H-(1,3,4)-oxadiazol-2-one

M.p.: 52° C.

Example 6

5-Octyloxy-3-phenyl-3H-(1,3,4)-oxadiazol-2-one

M.p.: 38° C.

Example 7

5-Octyloxy-3-(3-fluoro-phenyl)-3H-(1,3,4)-oxadiazol-2-one

M.p.: oil

Example 8

5-Hexadecyloxy-3-(3-fluoro-phenyl)-3H-(1,3,4)-oxadiazol-2-one

M.p.: 58° C.

Example 9

5-Hexadecyloxy-3-(3-benzyloxy-phenyl)-3H-(1,3,4)-oxadiazol-2-one

M.p.: 65° C.

Example 10

5-Hexadecyloxy-3-phenyl-3H-(1,3,4)-oxadiazol-2-one

M.p.: 63° C.

Example 11

5-Hexadecyloxy-3-(4-nitro-phenyl)-3H-(1,3,4)-oxadiazol-2-one

M.p.: 72° C.

Example 12

5-Hexadecyloxy-3-(4-methoxy-phenyl)-3H-(1,3,4)-oxadiazol-2-one

M.p.: 66° C.

Example 13

5-Hexadecyloxy-3-(4-benzyloxy-phenyl)-3H-(1,3,4)-oxadiazol-2-one

M.p.: 73° C.

Example 14

5-Decyloxy-3-(4-trifluoromethoxy-phenyl)-3H-(1,3,4)-oxadiazol-2-one

M.p.: oil

Example 15

5-Undecyloxy-3-(4-trifluoromethoxy-phenyl)-3H-(1,3,4)-oxadiazol-2-one

M.p.: 38° C.

Example 16

5-Tetradecyloxy-3-(4-trifluoromethoxy-phenyl)-3H-(1,3,4)-oxadiazol-2-one

M.p.: 46° C.

Example 17

5-Tridecyloxy-3-(4-trifluoromethoxy-phenyl)-3H-(1,3,4)-oxadiazol-2-one

M.p.: 50° C.

Example 18

5-(2-(2-Hexyloxy-ethoxy)-ethoxy)-3-(4-trifluoromethoxy-phenyl)-3H-(1,3,4)-oxadiazol-2-one M.p.: oil

Example 19

5-((Z)-Octadec-9-enyloxy)-3-(4-trifluoromethoxy-phenyl)-3H-(1,3,4)-oxadiazol-2-one M.p.: oil

Example 20

5-(Dodecyloxy-ethoxy)-3-(4-trifluoromethoxy-phenyl)-3H-(1,3,4)-oxadiazol-2-one

M.p.: oil

Example 21

5-(2-(4-Fluorophenyl)-ethoxy)-3-(4-trifluoromethoxy-phenyl)-3H-(1,3,4)-oxadiazol-2-one M.p.: 60° C.

Example 22

5-((3β-Cholestan-3-yl)-oxy)-3-(4-trifluoromethoxy-phenyl)-3H-(1,3,4)-oxadiazol-2-one M.p.: 127° C.

Example 23

5-(2-Butoxy-ethoxy)-3-(4-trifluoromethoxy-phenyl)-3H-(1,3,4)-oxadiazol-2-one

M.p.: resin

Example 24

5-(7-Phenyl-heptyloxy)-3-(4-trifluoromethoxy-phenyl)-3H-(1,3,4)-oxadiazol-2-one

M.p.: resin

Example 25

5-(Docosyloxy-ethoxy)-3-(4-trifluoromethoxy-phenyl)-3H-(1,3,4)-oxadiazol-2-one

M.p.: 71° C.

Example 26

5-(2-(1-Naphthyloxy)-ethoxy)-3-(4-trifluoromethoxy-phenyl)-3H-(1,3,4)-oxadiazol-2-one M.p.: resin

Example 27

5-(4-Octylphenoxy)-3-(4-trifluoromethoxy-phenyl)-3H-(1,3,4)-oxadiazol-2-one

M.p.: resin

Example 28

5-(3-Phenoxy-phenoxy)-3-(4-trifluoromethoxy-phenyl)-3H-(1,3,4)-oxadiazol-2-one

M.p.: resin

Example 29

5-(Dodecyloxy)-3-(4-trifluoromethoxy-phenyl)-3H-(1,3,4)-oxadiazol-2-one

M.p.: 41° C.

Example 30

5-(Dodecyloxy)-3-(3,4-dichloro-phenyl)-3H-(1,3,4)-oxadiazol-2-one

M.p.: 74° C.

Example 31

5-(Dodecyloxy)-3-(3,5-dichloro-phenyl)-3H-(1,3,4)-oxadiazol-2-one

M.p.: 48° C.

Example 32

5-(Dodecyloxy)-3-(3-methoxy-phenyl)-3H-(1,3,4)-oxadiazol-2-one

M.p.: 51° C.

Example 33

5-(Dodecyloxy)-3-(4-methoxy-phenyl)-3H-(1,3,4)-oxadiazol-2-one

M.p.: 57° C.

Example 34

5-(Dodecyloxy)-3-(3-nitro-phenyl)-3H-(1,3,4)-oxadiazol-2-one

M.p.: 64° C.

Example 35

5-(Dodecyloxy)-3-(3-trifluoromethyl-phenyl)-3H-(1,3,4)-oxadiazol-2-one

M.p.: 43° C.

Example 36

5-(Dodecyloxy)-3-(3,5-bis-trifluoromethyl-phenyl)-3H-(1,3,4)-oxadiazol-2-one

M.p.: oil

Example 37

5-(Dodecyloxy)-3-(4-benzyloxy-phenyl)-3H-(1,3,4)-oxadiazol-2-one

M.p.: 65° C.

Example 38

5-(Dodecyloxy)-3-(3-fluoro-phenyl)-3H-(1,3,4)-oxadiazol-2-one

M.p.: 44° C.

Example 39

5-(Dodecyloxy)-3-(3-(4-fluorobenzyloxy)-4-nitro-phenyl)-3H-(1,3,4)-oxadiazol-2-one M.p.: 71° C.

Example 40

5-(Dodecyloxy)-3-(2-methyl-4-nitro-phenyl)-3H-(1,3,4)-oxadiazol-2-one

M.p.: 63° C.

Example 41

5-(Dodecyloxy)-3-(3-methyl-4-nitro-phenyl)-3H-(1,3,4)-oxadiazol-2-one

M.p.: 62° C.

We claim:

1. A compound of formula I

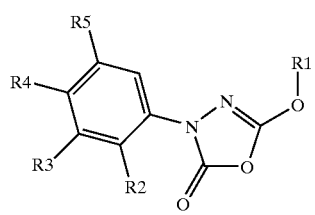

wherein:
R$^1$ is C$_7$–C$_{22}$-alkyl;
C$_4$–C$_{20}$-alkoxy-, C$_6$–C$_{10}$-aryl-, C$_6$–C$_{10}$-aryloxy- or C$_4$–C$_{12}$-alkoxy-C$_2$–C$_4$-alkoxy-substituted C$_2$–C$_4$- alkyl, wherein the $C_6$–$C_{10}$ aryl is a phenyl or naphthyl that is substitued one or more times by $C_1$–$C_8$-alkyloxy, nitro or $CF_3$, $C_7$–$C_{20}$-alkenyl;

3β-cholestan-3-yl; or phenyl that is substituted by phenoxy; and $R^2$, $R^3$, $R^4$ and $R^5$ are each, independently, hydrogen;

halogen;

nitro;

amino;

$CF_3$;

$OCF_3$;

$C_1$–$C_4$-alkyl, $C_1$–$C_9$-alkyloxy, $C_6$–$C_{10}$-aryl-$C_1$–$C_4$-alkyloxy, $C_6$–$C_{10}$-aryloxy, $C_6$–$C_{10}$-aryl, $C_1$–$C_4$-alkylamino, di-$C_1$–$C_4$-alkyl-amino, or $C_1$–$C_4$-alkylcarbonylamino, wherein the alkyl is optionally substituted one or more times by halogen, hydroxy, di-$C_1$–$C_4$-alkylamino, $CF_3$, $C_1$–$C_4$-alkyloxy or $C_1$–$C_4$-alkyl, and the aryl is optionally substituted one or more times by halogen, $C_1$–$C_9$-alkyl, $C_1$–$C_8$-alkyloxy or $CF_3$; or $C_3$–$C_8$-cycloalkyl or $C_3$–$C_8$-cycloalkyloxy, wherein the cycloalkyl is optionally substituted one or more times by halogen, $CF_3$, $C_1$–$C_4$-alkyloxy, $C_1$–$C_4$-alkyl or $C_6$–$C_{10}$-aryl;

or a prodrug, solvate, pharmaceutically acceptable basic salt or acid addition salt thereof.

2. A compound according to claim 1, wherein $R^1$ is $C_7$–$C_{22}$-alkyl, $C_7$–$C_{20}$-alkenyl, 3β-cholestan-3-yl, or phenyl that is substituted by $C_6$–$C_{12}$-alkyl or by phenoxy.

3. A compound according to claim 1, wherein $R^2$ is hydrogen, halogen, $C_1$–$C_4$-alkyl or $C_1$–$C_9$-alkyloxy.

4. A compound according to claim 1, wherein $R^3$ is hydrogen, $C_1$–$C_4$-alkyl, $OCF_3$, or $C_6$–$C_{10}$-aryl-$C_1$–$C_4$-alkyloxy, wherein the aryl is optionally substituted by halogen.

5. A compound according to claim 1, wherein $R^4$ is hydrogen, $OCF_3$ or chlorophenoxy.

6. A compound according to claim 1, wherein $R^5$ is hydrogen.

7. A compound according to claim 1, wherein:

$R^1$ is $C_7$–$C_{22}$-alkyl, $C_7$–$C_{20}$-alkenyl, 3β-cholestan-3-yl, or phenyl that is substituted by $C_6$–$C_{12}$-alkyl or by phenoxy;

$R^2$ is hydrogen, halogen, $C_1$–$C_4$-alkyl or $C_1$–$C_9$-alkyloxy;

$R^3$ is hydrogen, $C_1$–$C_4$-alkyl, $OCF_3$, or $C_6$–$C_{10}$-aryl-$C_1$–$C_4$-alkyloxy, wherein the aryl is optionally substituted by halogen;

$R^4$ is hydrogen, $OCF_3$ or chlorophenoxy; and $R^5$ is hydrogen.

8. A compound according to claim 1, wherein $R^1$ is $C_8$–$C_{16}$-alkyl.

9. A compound according to claim 1, wherein $R^1$ is $C_8$–$C_{16}$-alkyl;

$R^2$ is hydrogen;

$R^3$ is hydrogen or $OCF_3$;

$R^4$ is hydrogen, $OCF_3$ or 4-chlorophenoxy; and $R^5$ is hydrogen.

10. A pharmaceutical composition comprising at least one compound of formula 1 as claimed in claim 1 and a pharmaceutically acceptable carrier or excipient.

11. A method for the treatment of obesity, in a patient in need thereof, comprising administering to the patient a pharmaceutically effective amount of a compound of formula 1 as claimed in claim 1.

* * * * *